United States Patent [19]
Jennings et al.

[11] Patent Number: 5,795,580
[45] Date of Patent: Aug. 18, 1998

[54] GROUP B STREPTOCOCCUS TYPE V POLYSACCHARIDE-PROTEIN CONJUGATE VACCINES

[75] Inventors: Harold J. Jennings, Gloucester, Canada; Dennis L. Kasper, Newton Centre, Mass.

[73] Assignees: National Research Council of Canada, Ottawa, Canada; Brigham and Women's Hospital, Inc., Boston, Mass.

[21] Appl. No.: 483,647

[22] Filed: Jun. 7, 1995

Related U.S. Application Data

[63] Continuation of Ser. No. 125,556, Sep. 23, 1993, abandoned, which is a continuation-in-part of Ser. No. 949,970, Sep. 24, 1992, abandoned.

[51] Int. Cl.$^6$ ............................. A01J 21/00; A01J 17/00; C07K 1/00
[52] U.S. Cl. ............................. 424/244.1; 424/192.1; 424/194.1; 424/197.11; 424/203.1; 530/403
[58] Field of Search ............................. 424/192.1, 194.1, 424/197.11, 203.1, 244.1; 530/403, 813, 825

[56] References Cited

U.S. PATENT DOCUMENTS

| | | |
|---|---|---|
| 4,207,414 | 6/1980 | Kasper. |
| 4,324,887 | 4/1982 | Kasper. |
| 4,356,170 | 10/1982 | Jennings et al.. |
| 4,356,263 | 10/1982 | Kasper. |
| 4,425,330 | 1/1984 | Norcross et al. ............... 424/92 |
| 4,902,506 | 2/1990 | Anderson et al. ............... 424/92 |

FOREIGN PATENT DOCUMENTS

WO 91/04049  4/1991  WIPO.

OTHER PUBLICATIONS

Dick and Beurret (1989) "Glycoconjugates of Bacterial Carbohydrate Antigens — A Survey and Consideration of Design and Preparation Factors" Conjugate Vaccines In Contrib. Microbiol. Immunol. Cruse, JM and Lewis, RE. Tr. (eds.) Basel Karger Vol.10:48:114.

Jennings, (1983) "Capsular Polysaccharrides as Human Vaccines" In Advances Carbohydrate Chemistry and Biochemistry, Vol. 41:155–207. Academic Press, Inc., N.Y. NY.

Paoletti (1992) Effects of Chain Length on the Immunogenecity in Rabbits of Group B Streptococcus Type III Oligosaccharride — Tetanus Toxoid Conjugate. *J. Clin. Invest.* 89:203–209.

Paoletti (1992) "Group B Streptococcus Type II Polysaccharide —Tetanus Conjugate Vaccine" *Infection and Immunity*, vol. 60:4009–4014.

Michael R. Wessels, et al., (1989) "Isolation and Characterization of Type IV Group B Streptococcus Capsular Polysaccharide" *Infection and Immunity* vol. 57, No. 4:1089–1094.

Dennis L. Kasper, et al. (1983) "Immunochemical Analysis and Immunogenicity of the Type II Group B Streptococcals Capsular Polysaccharide ", *J. Clin. Invest.* vol. 72:260–269.

Harold J. Jennings, et al. (1982) "Structural Determination of the Capsular Polysaccharide Antigen of Type II Group B Streptococcus", *The Journal of Biological Chemistry*, vol. 258:1793–1798.

Lawrence C. Paoletti, et al. (1900) "An Oligosaccharide—Tetanus Toxoid Conjugate Vaccine against Type III Group B Streptococcus", *The Journal of Biological Chemistry*, vol. 265:18278–18283.

Ariane K. Rodewald, et al. (1992) "Neonatal Mouse Model of Group B Streptococcal Infection", *The Journal of Infectious Diseases*, vol. 166:635–9.

Wessels et al, J. Biol. Chem. 266(11): 6714–6719, 1991.

Ward et al, *"Haemophilus influenza* Vaccines" in *Vaccines*, Plotkin et al eds. W. B. Saunders Co. Philadelphia, 1988 pp. 300–330.

Facklam et al, "Streptococci and Aerococci" in *Manual of Clinical Microbiology*, Lennette et al eds. American Society for Microbiol, Wash DC 1985, pp. 154–175.

Baker et al, Reviews of Infectious Diseases 7(4): 458–467, 1985

Baker et al, New Engl. J. Med. 319 18: 1180–1185, 1988.

Sarvamangala et al, Proc. Natl. Acad. Sci. 88: 7175–7179, 1991.

Wessels et al, J Clin. Invest. 86: 1428–1433, 1990.

Boyer et al, Clinical Research 34(4): 962 A, 1986.

Jennings et al, Biochemistry, 20(16): 4511–4518, 1981.

Reuter et al, Glycoconjugate J. 6: 35–44, 1989.

*Primary Examiner*—James C. Housel
*Assistant Examiner*—Jennifer Shaver
*Attorney, Agent, or Firm*—Morgan & Finnegan, L.L.P.

[57] ABSTRACT

This invention relates to antigenic conjugate molecules comprising the capsular polysaccharide of Group B streptococcus type II which are covalently linked to protein. This invention further relates to antigenic conjugate molecules comprising the capsular polysaccharide of Group B streptococcus type V which are covalently linked to protein. This invention also relates to vaccines and methods of immunizing mammals, including humans against infection by Group B streptococcus type II (GBS II) and/or Group B streptococcus type V (GBS V). Multivalent vaccines comprising the conjugate molecules of this invention and antigens to other pathogenic bacteria are also claimed.

32 Claims, 6 Drawing Sheets

GROUP B STREPTOCOCCUS TYPE V POLYSACCHARIDE-PROTEIN CONJUGATE VACCINES

This is a continuation of application Ser. No. 08/125,556, now abandoned, filed on Sep. 23, 1993, which is a continuation-in-part of U.S. patent application Ser. No. 07/949,970 filed Sep. 24, 1992, now abandoned.

STATEMENT AS TO RIGHT TO INVENTION

This invention was made with Government support under NIH grant A123339, A130628 and A128040 awarded by the National Institutes of Health. The Government has certain rights in this invention.

FIELD OF THE INVENTION

This invention relates to antigenic conjugate molecules comprising the capsular polysaccharide of Group B streptococcus type II or V which are covalently linked to protein. This invention also relates to vaccines and methods of immunizing mammals, including humans against infection by Group B streptococcus type II (GBS II) and/or type V (GBS V). Multivalent vaccines comprising the conjugate molecules of this invention and antigens to other pathogenic bacterial are also claimed.

BACKGROUND OF THE INVENTION

Infections due to group B streptococci (GBS) are the most common single cause of sepsis and meningitis in newborns in developed countries (3, 31). Recent reports from some centers in the United States reflect a lower mortality (9 to 13%) than in series from the 1970s, perhaps as a result of earlier diagnosis and intensive care (1, 10). Nonetheless, fatal infections still occur, and equally important, up to 50% of survivors of GBS meningitis have chronic neurologic injury ranging from deafness and mild learning disabilities to profound motor, sensory, and cognitive impairment (3). Prevention rather than improved diagnosis or therapy is likely to have the most significant impact in further reducing GBS-related morbidity and mortality.

Because GBS capsular polysaccharide-specific antibodies appear to protect both experimental animals (23, 24) and human infants (4, 5) from GBS infection, some of the polysaccharides have been purified and tested in healthy adults as experimental vaccines (6). Were a safe and efficacious GBS vaccine available, it could be administered to women before or during pregnancy to elicit antibodies that would transfer to the fetus in utero and provide protection against neonatal infection. Of the three GBS polysaccharides (types Ia, II, and III) tested in volunteers, type II had the highest rate of immunogenicity, eliciting a type II-specific antibody response in 88% of previously nonimmune recipients (6). Although a variety of GBS serotypes have previously been recognized as contributing significantly to the percent of patients with GBS infection, type V has not been considered to be responsible for a significant percent of GBS infection. In neonates, the level of specific antibody required for protection against type II GBS infection is not precisely defined but has been estimated at 2 or 3 µg/ml (6). In a vaccine recipient who achieves an antibody response only slightly above the minimum required for protection, the amount of maternal antibody transferred across the placenta may be inadequate to protect a premature infant, because of the incomplete transfer to the fetus of material immunoglobulin G (IgG), or an infant with late-onset infection, since the half-life of maternal IgG antibodies in the newborn is about 25 days (13). Many of the infants in these two groups of patients might be protected if the magnitude of the specific antibody response to vaccination were higher. The transfer of maternal IgG to the fetus increases throughout the third trimester, so a higher maternal antibody level would provide protection earlier, i.e., to a more premature infant (16). Similarly, higher maternal levels would result in longer persistence of maternal antibodies in the infant, thereby providing protection against late-onset disease, as well.

The immunogenicity of several bacterial polysaccharide antigens has been increased by the attachment of suitable carrier proteins to polysaccharides or to derivative oligosaccharides (2, 14, 17–19, 22, 27, 29, 30, 34). Desirable properties of polysaccharide-protein conjugate vaccines include enhanced immunogenicity of the polysaccharide, augmented hapten-specific antibody response to booster doses, and a predominance of IgG class antibodies. Recently, we have been successful in developing a GBS III-Tetanus Toxoid (TT) vaccine by using the side chain sialic acid moieties as sites of directed protein coupling (33). The III-TT vaccine elicited GBS type III-specific, opsonically active antibodies, while the unconjugated type III polysaccharide was nonimmunogenic in rabbits (33).

SUMMARY OF THE INVENTION

This invention claims antigenic conjugate molecules comprising the capsular polysaccharide derived from Group B streptococcus type II and a protein component, or Group B streptococcus type V and a protein component, wherein two or more side chains terminating in sialic acid residues of the type II or type V polysaccharide component are each linked through a secondary amine bond to protein.

Also claimed is a method of preparing the conjugate molecules of a capsular polysaccharide of group B streptococcus type II or type V and a protein comprising:

(a) subjecting the Group B streptococcus type II or type V capsular polysaccharide to periodate oxidation sufficient to introduce an aldehyde group into two or more terminal sialic acid residues linked to the backbone of the polysaccharide;

(b) coupling the oxidized Group B streptococcus type II or type V capsular polysaccharide to a protein through reductive amination to generate a secondary amine bond between the capsular polysaccharide and the protein.

Conjugate molecules prepared according to the method described above are also claimed.

This invention further claims vaccines comprised of each of the conjugate molecules described above. In addition, this invention claims multivalent vaccines comprising the conjugate molecules of the invention and at least one other immunogenic molecule capable of eliciting the production of antibodies to a pathogenic substance other than Group B streptococcus type II or type V. In particular, in addition to comprising the GBS type II and/or GBS type V conjugate molecules,the multivalent vaccine, according to the invention, further comprises other immunogenic molecules capable of eliciting the production of antibodies to pathogens selected from the group consisting of Group B streptococcus types Ia, Ib, III, IV and Haemophilus influenzae type b and E. coli type K1.

In another embodiment of this invention, a method of immunizing neonates is claimed wherein the vaccine comprising the conjugate molecules of the invention are administered in an immunogenic amount to a female human so as to produce antibodies capable of passing into a fetus conceived prior to or after administration of the vaccine in an amount sufficient to produce protection against infection in the neonate at birth.

A method of immunizing adults wherein a vaccine comprising the conjugate molecules of the invention are administered in an immunogenic amount to a human adult is also claimed. In addition, a method of immunizing adults wherein a vaccine comprising the conjugate molecules of the invention are administered in an immunogenic amount to a person at risk for being infected by Group B streptococcus type II or type V is claimed.

In another embodiment of this invention, a vaccine comprising the conjugate molecules of the invention are administered in an immunogenic amount to volunteer vaccine recipients who could donate serum or plasma which could be passively administered to the above groups. This invention also provides a method of immunizing persons including neonates, children and adults at risk for being infected by Group B streptococcus type II or type V. Those at risk may include persons whose immune system is suppressed for a variety of reasons including but not limited to cancer or diabetes.

Another embodiment of this invention is a method of immunizing dairy herds against bovine mastitis consisting of administering a vaccine comprising the conjugate molecules of the invention in an immunogenic amount to dairy cows.

DESCRIPTION OF THE PREFERRED EMBODIMENTS

The invention relates to antigenic conjugate molecules comprising a capsular polysaccharide component and a protein component.

Bacterial strains. GBS type II strain 18RS21 and type Ia strain 090 were originally obtained from the late Rebecca Lancefield of Rockefeller University and were maintained as frozen cultures at −80° C. Strain 18RS21 was used in in vitro and in vivo assays and was the source of type II capsular polysaccharide used in the conjugate vaccine. Two GBS type II clinical isolates (strains S16 and S20) and type III strain M781 were obtained from the Channing Laboratory's culture collection.

Although previously not recognized as significantly contributing to the number of GBS infections in humans, recent evidence now indicates that the type V serotype contributes to about 15% of GBS infections. To prepare a GBS-type V conjugate vaccine, GBS type V strain 1169-NT1 were obtained from Dr. J. Jelinkova of The Institute of Hygiene And Epidemiology, Prague, Czech Republic and were maintained as frozen cultures at −80° C. Strain 1169-NT1 was used in in vitro and in vivo assays and was the source or type V capsular polysaccharide used in the conjugate vaccine. GBS type V strain CJB 111 was originally obtained from Dr. Carol Baker of Baylor University.

Conjugation of GBS type II polysaccharide or type V polysaccharide to TT. Type II capsular polysaccharide was purified from strain 18RS21 cells by methods described previously for purification of type III polysaccharide (33). The conjugation of type II polysaccharide to monomeric TT was performed by using techniques detailed previously for the conjugation of TT to GBS type III polysaccharide (33). In brief, native type II polysaccharide was size fractionated on a Sepharose CL-6B column (1.6 by 85 cm; Pharmacia Fine Chemicals). The material eluting at the center of the major peak was pooled, dialyzed against water, and lyophilized to yield material with a relative molecular weight of 200,000. Analysis of this material by $^1$H-nuclear magnetic resonance spectroscopy at 500 MHz confirmed the native type II polysaccharide structure (20) and the absence of group B antigen (26). Polysaccharides suitable for use in the conjugate molecules of this invention may vary in molecular weight over a broad range. A preferred molecular weight range for the polysaccharide component is between about 5,000 and 1,000,000 daltons. A more preferred range is between 100,000 and 300,000. Within the range of 100,000 to 300,000 daltons, polysaccharides having molecular weight of about 200,000 daltons are preferred.

The size-fractionated type II polysaccharide was subjected to mild oxidation with sodium meta-periodate (18). This procedure resulted in the conversion of a portion of the sialic acid residues on the polysaccharide to the eight-carbon analog of sialic acid, 5-acetamido-3,5-dideoxy-D-galactosyloctulosonic acid (33). The percentage of sialic acid residues oxidized was estimated by gas chromatography-mass spectroscopy of the sialic acid residues and their oxidized derivatives as described previously (33). Preferably between about 5 and 50% of the sialic acid residues of each GBS type II polysaccharide are modified and available to be linked to protein. Most preferably, between about 5 and 25% of the sialic acid residues of the GBS type II polysaccharide are modified and available for linkage to protein. Modification of between about 5 and 10% of the GBS type II polysaccharides is most preferred.

Oxidation of the GBS type V polysaccharide to achieve between about 5 and 80% modification of the terminal sialic acid residues to form reactive aldehydes is preferred. Modification of between about 10 to 50% of the terminal sialic acid residues is more preferred.

The protein component of the conjugate molecules of the invention may be any physiologically tolerated protein. Among the preferred proteins are tetanus toxoid, diptheria toxoid and cross reactive materials such as $CRM_{197}$.

The oxidized type II polysaccharide was linked to monomeric tetanus toxoid ("TT") (Institute Armand Frappier, Montreal, Canada) by reductive amination as described previously (33). The TT was purified to its monomer from by gel filtration chromatography also as described previously (33). In brief, 10 mg of the periodate-treated type II polysaccharide and 10 mg of purified TT were dissolved in 0.6 ml of 0.1M sodium bicarbonate (pH 8.1). Sodium cyanoborohydride (20 mg) was added to the mixture and incubated at 37° C. for 5 days. The progress of the conjugation was monitored by fast protein liquid chromatography (FPLC) of small aliquots of the reaction mixture analyzed on a Superose 6 (Pharmacia) gel filtration column. The reaction was terminated when the height of the peak eluting at the void volume of the column (representing the high-molecular-weight conjugate) remained constant. The conjugate was purified by chromatography on a column of Biogel A, 0.5M (Bio-Rad Laboratories, Richmond, Calif.) as described previously (33). The protein content of the vaccine was estimated by the method of Lowry et al. (25), with bovine serum albumin as a standard. The carbohydrate content was assessed by the method of Dubois et al. (11), with purified type II polysaccharide as a standard.

Type V capsular polysaccharide was purified from GBS type V strain 1169-NT1 cells by the methods described previously for the purification of type III polysaccharide (33). The conjugation of type V polysaccharide to monomeric TT was performed using techniques detailed previously for the conjugation of TT to GBS type III polysaccharide (33).

Native type V polysaccharide had a relative molecular weight of 200,000 Daltons. Analysis of this material by H-nuclear magnetic resonance spectroscopy at 500MHZ confirmed the native type V structure (2) and the absence of group B antigen (26).

To introduce reactive aldehyde groups at the terminal sialic acid residues of the type V polysaccharide for linking to protein, type V polysaccharide was subjected to mild oxidation with sodium meta-periodate (18). This procedure resulted in the conversion of a portion of the sialic acid residues on the polysaccharide to the eight-carbon analog of sialic acid, 5-acetimido-3,5-dideoxy-D-galactosyloctulosonic acid (33). The percentage of sialic acid residues oxidized was estimated by gas chromatography-mass spectroscopy of the sialic acid residues and their oxidized derivatives.

The oxidized type V polysaccharide was linked to monomeric TT (Institute Armand Frappier, Montreal, Canada) by reductive amination as described previously (33). The TT was purified to its monomer from by gel filtration chromatography also as described previously (33). In brief, 8.6 mg of the periodate-treated type V polysaccharide and 8.7 mg of purified TT were dissolved in 0.5 ml of 0.1M sodium bicarbonate (pH 8.2). Sodium cyanoborohydride (31.5 mg) was added to the mixture and incubated at 37° C. for 10 days. The progress of the conjugation was monitored by fast protein liquid chromatography (FPLC) of small aliquots of the reaction mixture analyzed on a Superose 6 (Pharmacia) gel filtration column. The reaction was terminated when the height of the peak eluting at the void volume of the column (representing the high-molecular-weight conjugate) remained constant. The conjugate was purified by chromatography on a 2.6×91 cm column of Sephacryl S-300 HR (Pharmacia) using 0.01M phosphate, 0.15M NaCl, pH7 plus 0.01% thimerosal as the running buffer. The protein content of the vaccine was estimated by the method of Lowry et al. (25), with bovine serum albumin as a standard. The carbohydrate content was assessed by the method of Dubois et al. (11), with galactose as a standard.

Vaccination of rabbits with II-TT vaccine and V-TT vaccine. Groups of three New Zealand White female rabbits (Millbrook Farms, Amherst, Mass.), each rabbit weighing approximately 3 kg, were vaccinated subcutaneously at four sites on the back with 50 µg of either uncoupled native type II polysaccharide or II-TT vaccine, each emulsified with complete Freund's adjuvant in a total volume of 2 ml. These animals received booster injections (50 µg) of vaccine prepared with incomplete Freund's adjuvant on days 20 and 41. Serum was obtained from each animal on days 0, 20, 34, 41, 55, and 70; filtered sterile; and stored at −80° C.

A New Zealand white female rabbit (Millbrook Farms, Amherst, Mass.) weighing approximately 3 kg was vaccinated subcutaneously at four sites on the back with 50 µg of GBS type V-TT conjugate vaccine mixed with alum in a total volume of 2 ml. This animal received booster injections (50 µg) of vaccine prepared with alum on days 22 and 42. Serum was obtained from each animal on days 0, 35, 56 and 91; filtered sterilized and stored at −80° C.

ELISAS. GBS type II-specific rabbit antibodies were quantified by enzyme-linked immunosorbent assay (ELISA) with goat anti-rabbit IgG conjugated to alkaline phosphatase (Tago Inc. Burlingham, Calif.) at 1/3,000 dilution. Microtiter plates (Immulon 2; Dynatech Laboratories, Inc., Chantillty, Va.) were coated with 100 ng of purified type II polysaccharide linked to poly-L-lysine per well as described before (15, 33). Antibody titers were recorded as the reciprocal dilution that resulted in an $A_{405}$ of $\geq 0.3$ when wells containing the reference serum (rabbit antiserum raised to whole BGS 18RS21 cells) at a dilution of 1/800 reached an $A_{405}$ of 0.5. The amount of antibody specific for the protein portion of the conjugate vaccine was estimated by ELISA by using plates coated with monomeric TT (100 ng per well). TT-specific IgG titers were recorded as the reciprocal dilution that resulted in an $A_{405}$ of $\geq 0.3$ 35 min after addition of the substrate, p-nitrophenyl phosphate (Sigma 104 phosphatase substrate tablets; Sigma Chemical Co.).

GBS type V-specific rabbit antibodies were also quantified by ELISA with goat anti-rabbit IgG conjugated to alkaline phosphatase (Tago Inc. Burlingham, Calif.) at 1/3,000 dilution. Microtiter plates (Immulon 2; Dynatech Laboratories, Inc., Chantillty, Va.) were coated with 100 ng of purified type V polysaccharide linked to poly-L-lysine per well as previously described (15). Antibody titers were recorded as the reciprocal dilution that resulted in an $A_{405}$ of $\geq 0.3$ when wells containing the reference serum (rabbit antiserum raised to whole type v strain 1169-NT1) at a dilution of 1/3000 reached an $A_{405}$ of 0.3.

Separation of IgG and IgM from Immune rabbit serum. Protein A-agarose affinity column chromatography (Pierce Chemical Co., Rockford, Ill.) was used to separate immunoglobulins (IgG and IgM) from 0.5 ml of pooled immune rabbit serum, obtained on day 70, raised to II-TT vaccine as described elsewhere (28). Separation of antibody classes was confirmed with type II polysaccharide-coated ELISA plates with goat anti-rabbit IgG γ and light chain specific; Tago) used at 1/500 dilution and goat anti-rabbit IgM (µ chain specific; Sera-Lab, Westbury, N.Y.) used at a 1/200 dilution.

Competitive ELISA. The specificity of rabbit serum raised to the II-TT vaccine was determined by competitive ELISA with homologous (type II) and heterologous (types Ia and III) polysaccharides as inhibitors. Epitope specificity of vaccine-induced pooled rabbit serum (obtained on day 70) was examined with native and desialylated type II polysaccharide and β-O-methylgalactopyranose as inhibitors of antibody binding. Native type II polysaccharide was desialylated by treatment with 6% acetic acid at 80° C. for 2 h. Polysaccharide inhibitors were serially diluted 4-fold and mixed with an equal volume (75 µl) of pooled rabbit serum (diluted 10,000-fold) obtained on day 70 after vaccination with II-TT vaccine. This mixture (100 µl) was then added to type II polysaccharide-coated ELISA wells. Alkaline phosphatase-conjugated anti-rabbit IgG was used as the secondary antibody at a dilution of 1/3,000. Results are expressed as follows: % inhibition=|$A_{405}$ with no inhibitor-$A_{405}$ with inhibitor|/$A_{405}$ with no inhibitor|×100.

The serotype specificity of GBS V-TT rabbit antiserum was evaluated using GBS type-specific polysaccharides Ia, Ib, II, III, V and VI. ELISA wells were coated with 100 ng/well with GBS type V polysaccharide linked to poly-L-lysine. Rabbit antisera to V-TT vaccine, diluted 1/6,000, was incubated with each of the polysaccharide inhibitors. Incubated antiserum was added to ELISA wells and the plate processed with goat anti-rabbit IgG alkaline phosphatase conjugate (diluted 1/3000), and substrate as detailed previously (28).

In vitro antibody-mediated killing of GBS. The ability of vaccine-induced rabbit antibodies to opsonize GBS cells for subsequent killing by human peripheral blood leukocytes was assessed by an in vitro opsonophagocytosis assay (7, 8).

The reaction assay for determining the opsonophagocytic activity of GBS type V reactive antibodies was conducted by incubating $1.5 \times 10^7$ white blood cells (WBC) in 300 µl of buffer; $3 \times 10^6$ CFU of type V GBS stain CJB 111 in 50 µl; human complement (absorbed with GBS type V strain cells) (50 µl); antibody-anti V-TT-heat inactivated (50 µl); modified Eagle's Medium (50 µl). The mixture was incubated with mixing for 60 min at 37° C. The difference in GBS Colony Forming Units (CFU) was determined following incubation at 37° C. for 1 hour by the standard plate count method.

Passive protection of mice by vaccine-induced rabbit antibodies. Groups of 10 Swiss-Webster outbred female mice (Taconic Farms, Germantown, N.Y.), each mouse weighing 18 to 20 g, were injected intraperitoneally with 0.2 ml of pooled serum (day 70) from rabbits vaccinated with either type II polysaccharide or II-TT vaccine. The titer, as measured by ELISA, of the pooled serum obtained on day 70 from rabbits immunized with type II polysaccharide was 100, and that of II-TT vaccine was 12,800. Control groups of five mice received pooled preimmunization rabbit serum or pooled antiserum raised to uncoupled TT (27). Twenty-four hours later, mice were challenged with type II strain 18RS21 ($1.5 \times 10^5$ CFU per mouse) in a total volume of 1.0 ml of Todd-Hewitt broth. The challenge dose for each strain was previously determined to be lethal for >90% of mice of similar weights and ages. Surviving mice were counted daily for three subsequent days.

Statistical Analysis. Fisher's exact test was used to compare the abilities of different rabbit sera to passively protect mice against lethal GBS infection.

RESULTS

Preparation and composition of II-TT vaccine and V-TT vaccine. GBS II-TT vaccine and GBS V-TT vaccine were prepared by methods detailed previously for the construction of the GBS type III conjugate vaccine (33). Controlled periodate oxidation of type II GBS polysaccharide resulted in the modification of 7% of the polysaccharide's sialic acid residues as determined by gas chromatography-mass spectrometry analysis. Monomeric TT was covalently linked to modified sialic acid sites on the type II polysaccharide by reductive amination. The purified II-TT vaccine contained 32% (wt/wt) protein and 68% (wt/wt) carbohydrate. The final yield of II-TT vaccine was 7.8 mg, or 39%.

Controlled periodate oxidations of type V GBS polysaccharide resulted in modification of about 8%, 25% and 50% of the sialic acid residues in the polysaccharide. Monomeric TT was covalently linked to the modified sialic acid residues on the type V polysaccharide by reductive amination. Polysaccharides oxidized so that about 8% of their sialic acid residues were modified, resulted in conjugates having a low polysaccharide to protein molar ratio. Polysaccharides in which 25 or 50% of the terminal sialic acid residues were modified resulted in conjugate molecules having a more preferred polysaccharide to protein molar ratio. A GBS type V polysaccharide in which 25% of the sialic acid residues were modified, was used to produce conjugate vaccines having the biochemical characterization shown in Table I.

TABLE 1

| Composition of the GBS type V-TT Vaccine | |
|---|---|
| Polysaccharide size ($M^r$) | 200,000 |
| Sialic acid residues oxidized (%) | 25 |
| Amount of vaccine as tetanus toxoid (% dry wt.) | 38 |
| Amount of vaccine as carbohydrate (% dry wt.) | 62 |
| Mol carbohydrate/mol protein[a] | 0.56 |

[a]Determined $M^r$ of tetanus toxoid monomer was 150,000.

Immunogenicity of II-TT vaccine and V-TT vaccine in rabbits. The immunogenicities of the II-TT vaccine and native type II polysaccharide were compared in rabbits. An increase in type II-specific antibody was seen following the primary dose of II-TT vaccine (Table 2). A booster dose of vaccine further increased the antibody response. Antibody levels remained unchanged or rose slightly following a second booster, dose on day 41 and were sustained throughout the remainder of the study (Table 2). In contrast to the II-TT vaccine, uncoupled native GBS type II polysaccharide failed to elicit a specific antibody response (Table 2). Animals vaccinated with the II-TT vaccine also developed antibodies to TT, achieving approximately a 3-$\log_{10}$ increase over preimmunization levels.

TABLE 2

GBS type II polysaccharide-specific antibody titers of rabbits vaccinated with native type II polysaccharide or II-TT vaccine

| Vaccine and rabbit | Antibody titer in ELISA as day:[a] | | | | | |
|---|---|---|---|---|---|---|
| | 0 | 20[b] | 34 | 41[b] | 55 | 70 |
| Native type II poly-saccharide | | | | | | |
| 1 | 100 | 100 | 100 | 200 | 100 | 100 |
| 2 | 100 | 100 | 100 | 100 | 100 | 100 |
| 3 | 200 | 100 | 100 | 100 | 100 | 100 |
| II-TT | | | | | | |
| 1 | 100 | 400 | 3,200 | 3,200 | 6,400 | 12,800 |
| 2 | 100 | 1,600 | 3,200 | 6,400 | 6,400 | 25,600 |
| 3 | 100 | 6,400 | 12,800 | 25,600 | 12,800 | 12,800 |

[a]A value of 100 indicates an antibody titer of ≦100. Values are the means of duplicate determinations. Rabbits were vaccinated subcutaneously with 50 µg of vaccine emulsified with complete Freund's adjuvant on day 0.
[b]Booster doses with incomplete Freund's adjuvant were administered.

The immunogenicity of the V-TT vaccine (polysaccharide oxidized to 25%) was also assessed in rabbits. Antibody (IgG) levels increased following the first and second dose of type V-II vaccine and were sustained for the course of the study (Table 3).

TABLE 3

GBS type V polysaccharide-specific IgG titer.

| Vaccine | IgG titer as determined by an ELISA at day[a]: | | | |
|---|---|---|---|---|
| | 0 | 35 | 56 | 91 |
| $V_{25\%oo}$-TT Rabbit 1[a] | 100 | 800 | 1,600 | 1,600 |

[a]This animal received three-50 µg doses of vaccine mixed with alum at 3 week intervals beginning at day 0

Figure 1:
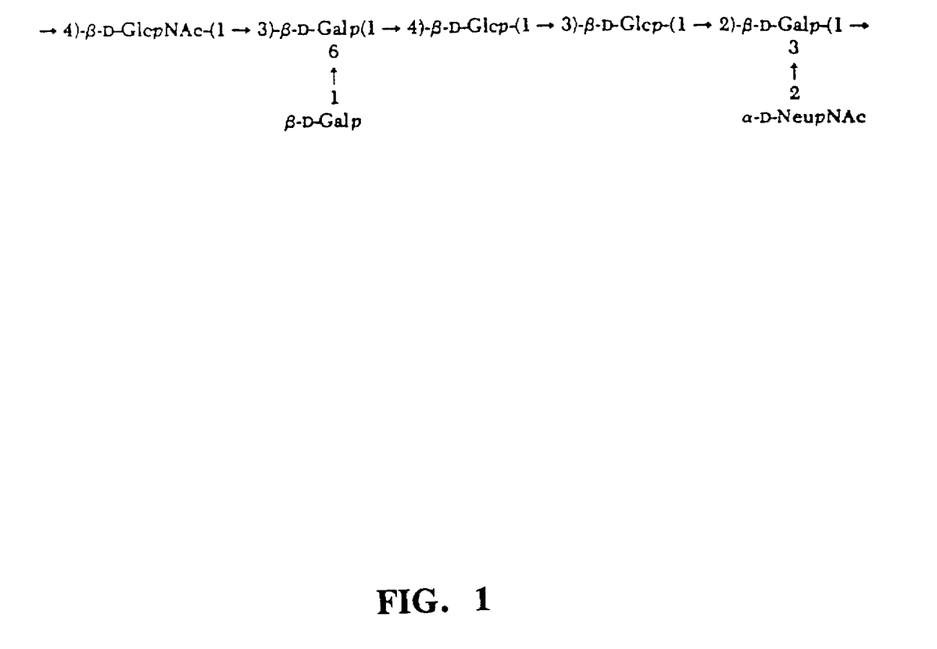
FIG. 1. Structure of the heptasaccharide repeating unit of type II GBS capsular polysaccharide 920).
Figure 2:
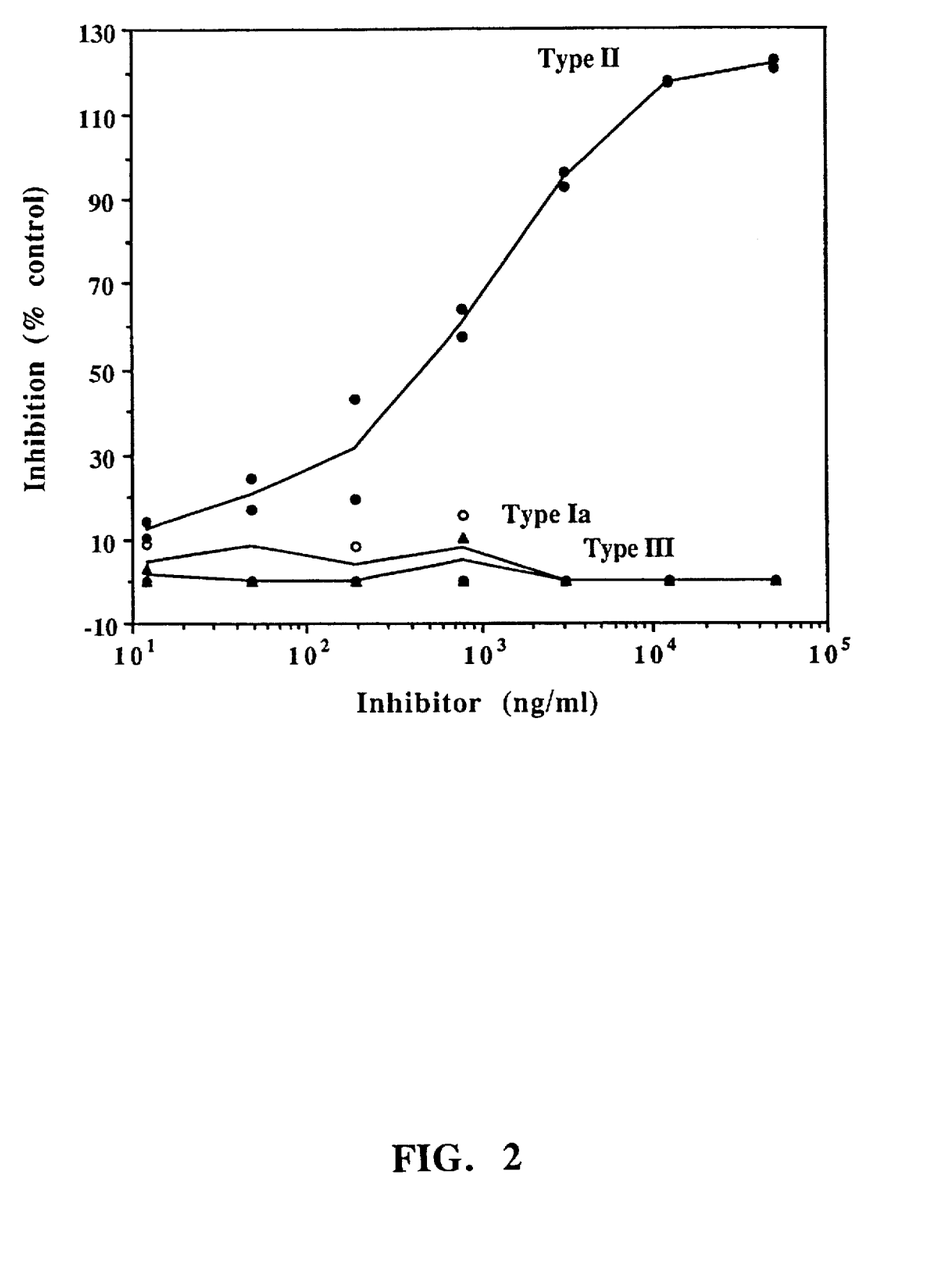
FIG. 2. GBS type II polysaccharide competitive ELISA. GBS type Ia (○), type II (●), and type III (▲) polysaccharides were used as inhibitors of II-TT vaccine antibody binding to plates coated with type II polysaccharide. Results are expressed as percentages of inhibition relative to that of control wells that lacked inhibitor.

Antigenic properties of vaccine-induced rabbit sera. The conjugation of polysaccharide to a protein carrier should not alter important antigenic epitopes found on the polysaccharide in its native form. We tested the specificity of II-TT vaccine-induced antibodies by competitive ELISA using homologous and heterologous GBS polysaccharides as inhibitors. Native type II polysaccharide at a concentration of 450 ng/ml inhibited 50% of the binding of rabbit antibodies raised to II-TT vaccine (FIG. 2). GBS type Ia and type III polysaccharides did not inhibit binding of serum raised to II-TT vaccine even at concentrations as high as 500 µg/ml. (FIG. 2). These result verify the serotype specificity of II-TT vaccine-induced antibodies for the target antigen and indicate preservation of antigenic epitopes of the polysaccharide portion of the conjugate vaccine.

Figure 3:
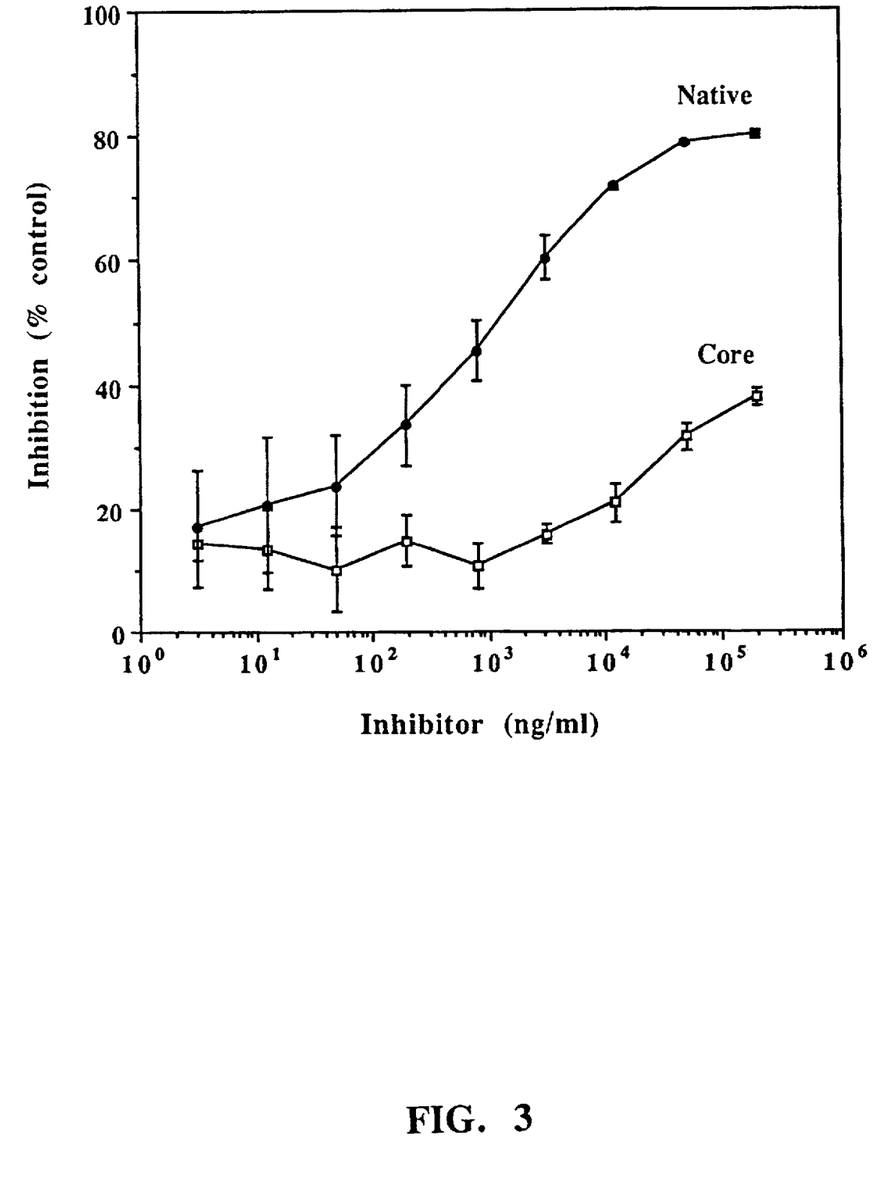
FIG. 3. GBS type II polysaccharide competitive ELISA. Native (●) and desialylated or core (□) type II polysaccharides were used as inhibitors of antibodies elicited by II-TT vaccine. Datum points are means (with standard deviations) of triplicate determinations. Results are expressed as percentage of inhibition relative to that of control wells that lacked inhibitor.

To determine whether the epitope influenced by sialic acid was maintained during the preparation of II-TT vaccine, native and desialylated type II polysaccharides were used in a competitive ELISA as inhibitors of binding of rabbit antibodies raised to II-TT vaccine. Desialylation of the polysaccharide was accomplished by treatment with 6% acetic acid at 80° C. for 2 h. Quantitative removal of sialic acid residues was confirmed by the thiobarbituric acid assay (32) with N-acetylneuraminic acid (Sigma) as the standard. The $K_{av}$ of native type II polysaccharide before acid treatment was 0.49, whereas the $K_{av}$ of acid-treated polysaccharide was 0.52 on a Superose 6 FPLC column (LKB-Pharmacia, Sweden), indicating a slight reduction in molecular size of the polysaccharide due to the loss of the side chain sialic acid residues that make up 20% of the native polysaccharide by weight. Even 200 µg of desialylated GBS type II polysaccharide per ml inhibited by 33% of the binding of II-TT vaccine antibodies to native type II polysaccharide (FIG. 3). The relatively poor recognition of the desialylated or core type II polysaccharide by II-TT vaccine antiserum was confirmed by immunoelectrophoresis gels, which showed a precipitin band formed with the native but not the core type II polysaccharide (not shown). Binding of II-TT vaccine antisera to native type II polysaccharide could not be inhibited with β-O-methylgalactopyranose used at a concentration range of 0.01 to 10 mg/ml (not shown).

Figure 5:
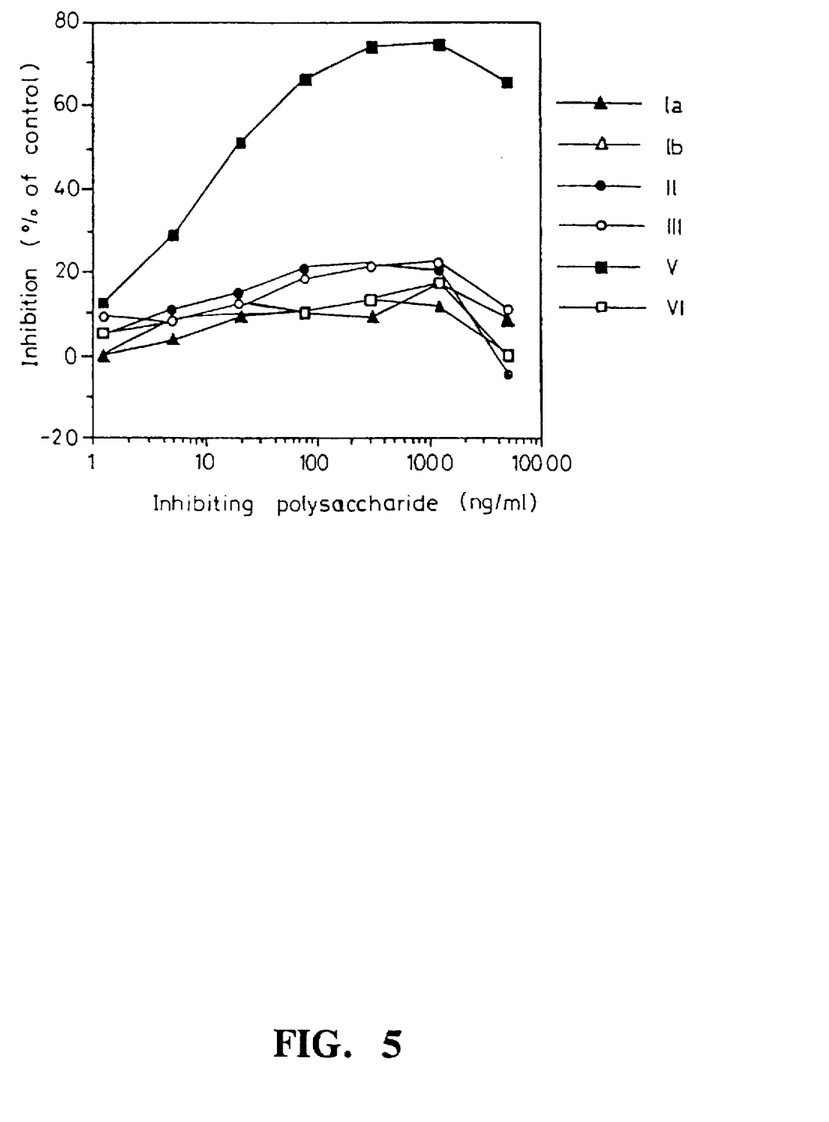
FIG. 5. GBS type V polysaccharide competitive ELISA. GBS type Ia (-▲-) type Ib (-●-), type II (-■-), type III (-○-), type V (-■-), and type VI (-□-) polysaccharides were used as inhibitors of antibodies elicited by V-TT vaccine. Datum points are means of duplicate determinations. Results are expressed as percentage of inhibition relative to that of control wells that lacked inhibitor.

The specificity of GBS type V-TT vaccine-induced antibodies was tested by competitive ELISA using homologous and heterologous GBS polysaccharides as inhibitors. Native type V polysaccharide effectively inhibited binding of rabbit antibodies raised to type V-TT vaccine (FIG. 5). GBS type Ia, type Ib, type II, type III an type VI did not inhibit binding of serum raised to type V-TT vaccine (FIG. 5). These results demonstrate the specificity of type V-TT vaccine induced antibodies for the target antigen.

In vitro activity of GBS vaccine-induced antibodies. The ability of immune serum to opsonize GBS for killing by human peripheral blood leukocytes in vitro has correlated with protective efficacy against GBS in animal protection experiments (27, 33). Antibodies raised in the three rabbits vaccinated with II-TT vaccine enhanced the killing of GBS type II strain 18RS21 by ≧1.8 $\log_{10}$ (Table 4). Preimmunization rabbit serum or serum from rabbits vaccinated with native GBS type II polysaccharide or uncoupled TT failed to enhance the in vitro killing of GBS (Table 4). Vaccine-induced rabbit antibodies promoted the killing by human blood leukocytes of two GBS type II clinical isolates (strains S16 and S20) by ≧1.8 $\log_{10}$ compared with preimmunization rabbit serum (Table 5). Rabbit serum to type II-TT vaccine was determined to be serotype specific, as it failed to promote the in vitro killing of heterologous (types Ia and III) GBS strains (Table 5).

TABLE 4

In vitro opsonophagocytic killing of GBS type II strain 18RS21 by rabbit antiserum raised to native type II polysaccharide, II-TT vaccine, or TT

| Serum source (day of collection) | CFU at[a]: | | GBS killed ($\log_{10}$) |
|---|---|---|---|
| | 0 min | 60 min | |
| Type II polysaccharide (70)[b] | $4.3 \times 10^6$ | $6.6 \times 10^6$ | −0.19 |
| II-TT vaccine (0) | $6.0 \times 10^6$ | $6.4 \times 10^6$ | −0.03 |
| II-TT vaccine (70) | | | |
| Rabbit 1 | $4.0 \times 10^6$ | $5.7 \times 10^4$ | 1.85 |
| Rabbit 2 | $4.3 \times 10^6$ | $2.7 \times 10^4$ | 2.20 |
| Rabbit 3 | $3.9 \times 10^6$ | $4.3 \times 10^4$ | 1.96 |
| TT (70) | $4.2 \times 10^6$ | $6.9 \times 10^6$ | −0.21 |
| None | $3.9 \times 10^6$ | $7.1 \times 10^6$ | −0.26 |

[a]Reaction mixture contained serum (at a final assay concentration of 1%) to be tested, type II GBS-absorbed human serum as a source of complement, human peripheral blood leukocytes, and type II GBS 18RS21. Values are means of duplicate determination.
[b]Rabbit serum collected following the primary dose of native type II polysaccharide in complete Freund's adjuvant.

TABLE 5

In vitro opsonophagocytic killing of GBS strains by preimmunization and immune rabbit serum raised to II-TT vaccine

| GBS type and strain | GBS killed ($\log_{10}$)[a] | |
|---|---|---|
| | Preimmunization (day 0) | Immune II-TT vaccine (day 70) |
| II | | |
| 18RS21 | −0.36 | 1.98 |
| S16 | 0.96 | 2.78 |
| S20 | −0.01 | 1.84 |
| Ia 090 | ND | −0.51 |
| III M781 | ND | −0.54 |

[a]CFU ($\log_{10}$) at 60 min–CFU ($\log_{10}$) at 0 min. Reaction mixture contained serum to be tested, type II GBS-absorbed human serum as a source of complement, human peripheral blood leukocytes, and type II GBS 18RS21. Values are means of duplicate determinations. ND, not done.

Protein A-affinity-purified IgG and IgM were obtained from pooled serum raised to type II-TT vaccine (28). The specificity of each Ig fraction was confirmed by ELISA with class-specific secondary antibody. The $A_{405}$S of the IgM and IgG fractions (diluted 1/100) were 0.384 and 0.009, respectively, with µ-chain-specific conjugate and 0.086 and 2.367, respectively, with goat anti-rabbit IgG (γ and light chain specific). Isolated IgM and IgG were tested for their abilities to enhance opsonic killing of type II GBS by human blood leukocytes. Unfractionated sera raised to type II-TT vaccine diluted 1:100 and an equivalent 1:100 dilution of the IgG fraction from the same sera promoted killing of type II GBS by 1.65±0.22 and 0.95±0.09 $\log_{10}$, respectively. In contrast, type II GBS were not killed but grew in the presence of preimmunization serum ($-0.39\pm0.13$ $\log_{10}$) and IgM-enriched fraction from serum raised to type II-TT vaccine ($-0.28\pm0.09$ $\log^{10}$) in the opsonophagocytic assay.

Figure 6:
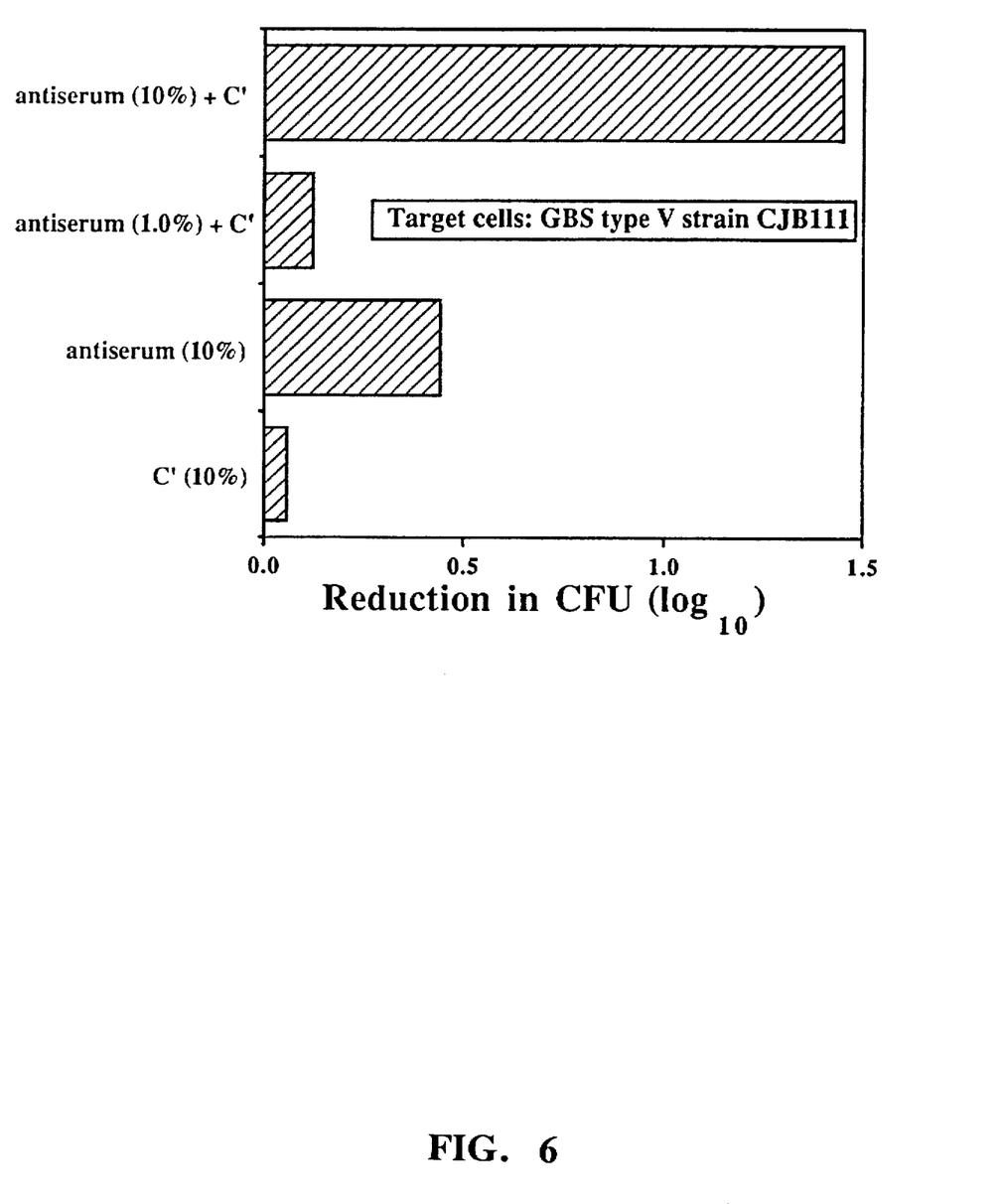
FIG. 6. In vitro opsonophagocytic killing by human peripheral blood lymphocytes of GBS type V strain CJB 111 opsonized by rabbit antisera raised to GBS type V-TT conjugate vaccine. C' is complement.

The ability of GBS type V-TT vaccine-induced rabbit antisera to promote the killing of a GBS-type V strain (CJB 111) by human blood leukocytes was also assessed by the in vitro opsonophagocytic assay (8). As shown in FIG. 6, GBS type V-TT antisera at a concentration of 10%, effectively optimized GBS type V strain CJB 111 relative to controls. Control reactions conditions were: complement (10%) without antisera; antiserum (10%) without complement; antiserum (1%) and complement.

Mouse protection assay. To test the in vivo protective abilities of vaccine-induced antibodies, mice were passively immunized with pooled II-TT vaccine sera (day 70) 24 h prior to challenge with type II GBS 18RS21. Previously, the challenge does was determined to be lethal for 90 to 100% of mice tested. Complete (100%) protection was afforded to groups of mice that received serum raised to GBS II-TT vaccine, whereas only one of five mice receiving prevaccination serum survived (Table 6). There were no survivors among mice that received serum from rabbits vaccinated with either uncoupled type II polysaccharide or uncoupled TT (Table 6).

TABLE 6

Passive protection of Swiss-Webster outbred mice against GBS type II strain 18RS21 with sera from rabbits vaccinated with native type II polysaccharide II-TT vaccine, or TT[a]

| Rabbit serum[b] (day of collection) | No. of survivors/ total no. of mice[c] | % Survival |
|---|---|---|
| II-TT vaccine (70) | 10/10 | 100[d] |
| II-TT vaccine (0) | 1/5 | 20 |
| Type II polysaccharide (70) | 0/10 | 0 |
| TT (70) | 0/5 | 0 |

[a]Mice were given a 90% lethal dose (1.5 × 10⁵ CFU per mouse) of GBS.
[b]Serum samples from three rabbits were pooled.
[c]Survival was determined 72 h after challenge.
[d]$P = 0.0037$ compared with preimmunization (day 0) values.

The coupling strategy used with GBS type III polysaccharide, first developed for meningococcal polysaccharide (18), may be applicable to all GBS capsular polysaccharide antigens, since they all contain sialic acid. However, unlike the other GBS polysaccharides that have sialic acid as the terminal saccharide of di-or trisaccharide side chains, the GBS type II polysaccharide has a repeating unit that bears sialic acid as the sole sugar on one of the two monosaccharide side chains (9, 20). In constructing the GBS type II conjugate vaccine, we oxidized 7% of sialic acid residues on the type II polysaccharide and used these as sites for coupling the polysaccharide to TT. Purified II-TT vaccine eluted in the void volume of a Superose 6 column (compatible with a molecular weight of $>10^6$) and was composed of 68% (wt/wt) carbohydrate and 32% (wt/wt) protein.

Type II-TT vaccine emulsified with adjuvant was immunogenic in rabbits in contrast to uncoupled native type II polysaccharide, which failed to elicit type II polysaccharide-specific antibody. Two of three rabbits immunized responded strongly 3 weeks after a single dose of II-TT vaccine. Optimal type-specific antibody was achieved in all three rabbits 3 weeks after a booster dose of II-TT vaccine. Further increases in type II-specific antibody titer were not seen after the third dose of II-TT vaccine. Results from in vitro and in vivo experiments indicated that antibodies raised to II-TT vaccine were functionally active against type II GBS. Serum from each of three rabbits vaccinated with II-TT vaccine promoted the in vitro killing of type II GBS by human peripheral leukocytes and provided outbred mice with complete (100%) protection against a lethal dose of type II GBS. II-TT vaccine antiserum was opsonically active against homologous GBS strains (18RS21, S16, and S20) but not heterologous GBS serotypes (types Ia and III) tested.

Whereas native type II polysaccharide inhibited binding of II-TT vaccine antisera to type II polysaccharide-coated ELISA wells, <40% inhibition was obtained with desialylated type II polysaccharide, even when it was used at a concentration of 200 µg/ml. This result suggests that an important antigenic determinant of type II polysaccharide is dependent on the presence of sialic acid residues. This result corroborated those obtained with rabbit antisera raised to whole type II organisms (21). However, ELISA inhibition experiments using β-O-methylgalactopyranose as an inhibitor indicated that rabbit antisera raised to II-TT vaccine did not contain galactose-specific antibodies. No inhibition of binding of II-TT vaccine antiserum to type II native polysaccharide was obtained even with β-O-methylgalactopyranose at a concentration of 10 mg/ml. Therefore, the side chain galactose does not appear to be an immunodominant epitope of type II polysaccharide when the polysaccharide is coupled to TT. These results are in contrast to immunochemical studies performed with rabbit sera raised to whole type II GBS organisms (12, 21) in which the galactose side chain appeared to be one of two immunodominant sites, along with a sialic acid-dependent epitope, of type II polysaccharide. Whole type II GBS cells used in previous studies (12, 21) and not cultured in pH-controlled conditions may possess polysaccharides that, to some degree, lack sialic acid. Under these circumstances, the side chain galactose might be major antigenic epitope. The source of type II polysaccharide used to synthesize the II-TT vaccine was a culture of type II GBS maintained at a pH of 7.0; a final analysis confirmed that sialic acid constituted ~20% (wt/wt) of the polysaccharide. We cannot exclude the possibility that coupling type II polysaccharide to TT altered the conformation of the polysaccharide, thereby rendering the galactose epitope unavailable for recognition by the host immune system. Although II-TT vaccine-induced rabbit antiserum lacked galactose-specific antibodies, it was fully functional in vitro and in vivo against type II GBS organisms. Neither chemical modification of some of the sialic acid residues nor the subsequent binding of TT to these sites altered critical antigenic epitopes necessary to elicit functional type II-specific antibody. That purified IgG from rabbit sera raised to II-TT vaccine promoted killing in vitro of type II GBS by human leukocytes suggests that not only was the immunogenicity of type II polysaccharide increased by conjugating it to TT but also that functional IgG antibodies were elicited.

Figure 4:
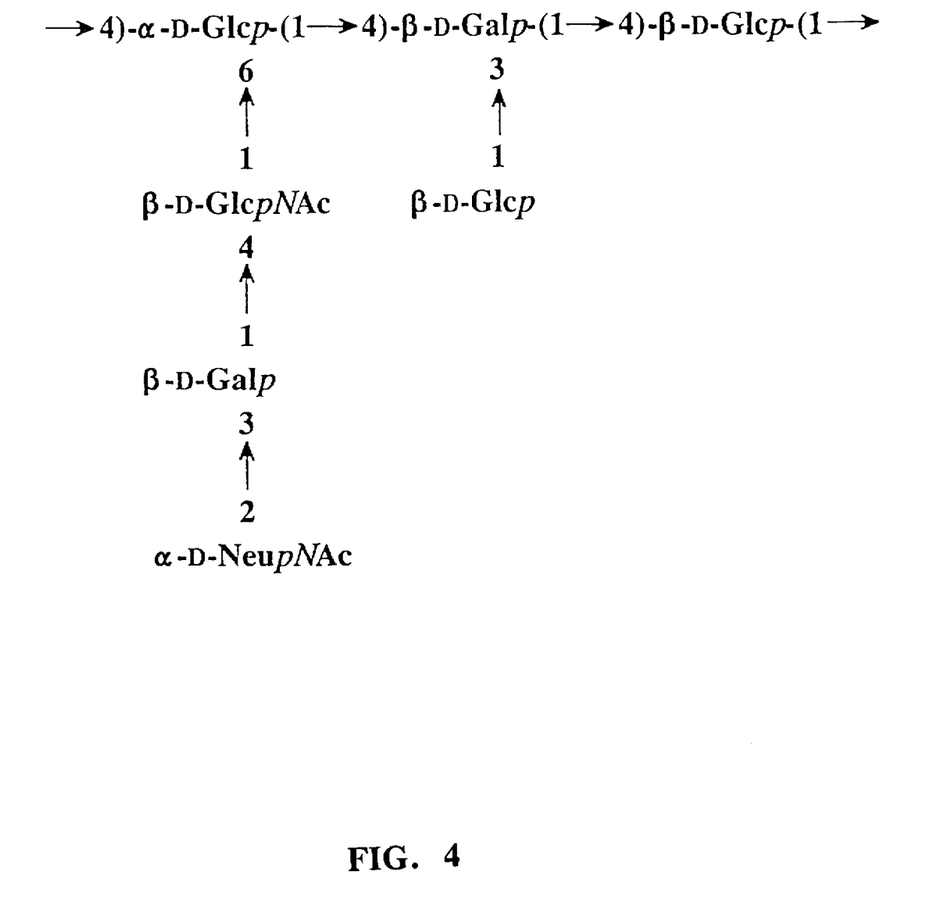
FIG. 4. Structure of the repeating unit of type V GBS capsular polysaccharide.

The GBS type V capsular polysaccharide has a repeating unit structure consisting of a trisaccharide backbone containing two distinct side chains on adjacent sugar residues. (Reference 35; FIG. 4). In one of the GBS type V-TT conjugate vaccine preparations, 25% of the sialic acid residues on the longer side chain (i.e. 3 sugar residues) in the type V polysaccharide were oxidized. The oxidized sialic acid residues were used as sites to couple the type V polysaccharide to TT. The purified type V-TT vaccine was composed of 38% (wt/wt) TT and 62% (wt/wt) carbohydrate. The V-TT vaccine mixed with alum was shown to be immunogenic in rabbits. A strong response was observed after the first dose and booster doses of type V-TT vaccine. The second booster dose also resulted in a further increase in the type V polysaccharide IgG titer. The serospecificity of the type V-TT induced assays was demonstrated by competitive ELISAs. Rabbit antiserum raised against the V-TT vaccine are functionally active as evidenced by the ability to kill type V GBS in vitro in the presence of human white blood cells and complement.

Like III-TT vaccine, II-TT vaccine demonstrated improved immunogenicity in rabbits compared with active polysaccharide and elicited opsonically active IgG in rabbits despite difference in polysaccharide structure, position of the sialic acid on the polysaccharide to which TT was linked, and vaccine composition. The type V-TT vaccine also proved immunogenic in rabbits and to be capable of inducing functionally antibodies in vivo. We anticipate that GBS polysaccharide-protein conjugates of this design will ultimately constitute components of a multivalent GBS vaccine capable of providing protection against the GBS serotypes most often associated with disease in humans.

In addition, we anticipate that vaccines can be produced from the conjugate molecules of this invention, by adding the conjugate molecules to a pharmaceutically acceptable carrier. Preferably, the degree of crosslinking in the antigenic molecules of this invention is controlled to an extent sufficient to provide vaccines which may be filter sterilized through a 0.2 micron filter. Such vaccines preferably are soluble. Immunization may be effected by injecting the recipient mammal with the vaccine once followed by subsequent booster injections as necessary. A sufficient dose of the vaccine to be administered can be based on the amount of polysaccharide present: a range of 3–80 µg of the polysaccharide component of the conjugate vaccine may be administered.

REFERENCES

1. Adams, W. G., J. Kinney, A. Schuchat, C. Collier, C. Papasian, H. Kilbride, F. Riedo, and C. Broome. 1991, Program Abstr. 31st Intersci. Conf. Antimicrob. Agents Chemother., abstr. 1056.
2. Avery, O. T., and W. F. Goebel. 1931. Chemo-immunological studies on conjugated carbohydrate-proteins. V. The immunological specificity of an antigen prepared by combining the capsular polysaccharide of type III pneumococcus with foreign protein. J. Exp. Med. 54:437–447.
3. Baker, C. J., and M. S. Edwards. 1990. Group B streptococcal infections, p. 742–811, In J. S. Remington and J. O. Klein (ed.), Infectious diseases of the fetus and newborn infant. The W. B. Saunders Co., Philadelphia.
4. Baker, C. J., M. S. Edwards, and D. L. Kasper. 1981. Role of antibody to native type III polysaccharide of group B Streptococcus in infant infection, Pediatrics 68:544–549.
5. Baker, C. J., and D. L. Kasper. 1976. Correlation of material antibody deficiency with susceptibility to neonatal group B streptococcal infection, N. Engl. J. Med. 294:753–756.
6. Baker, C. J., and D. L. Kasper. 1985. Group B streptococcal vaccines. Rev. Infect. Dis. 7:458–467.
7. Baker, C. J., M. A. Rench, M. S. Edwards, R. J. Carpenter, B. M. Hays, and D. L. Kasper. 1988. Immunization of pregnant women with a polysaccharide vaccine of group B Streptococcus. N. Engl. J. Med. 319:1180–1220.
8. Baltimore, R. S., D. L. Kasper, C. J. Baker, and D. K. Goroff. 1977. Antigenic specificity of opsonophagocytic antibodies in rabbit anti-sera to group B streptococci. J. Immunol. 118:673–678.
9. De Cueninck, B. J., T. F. Grebar, T. K. Eisenstein, R. M. Swenson, and G. D. Schockman. 1983. Isolation, chemical composition, and molecular size of extracellular type II and type Ia polysaccharides of group B, streptococci. Infect. Immun. 41:527–534.
10. Dillon, H. C., S. Khare, and B. M. Gray. 1987. Group B streptococcal carriage and disease: a six-year retrospective study. J. Pediatr. 110:31–36.
11. Dubois, M., K. A. Gilles, J. K. Hamilton, P. A. Rebars, and F. Smith. 1956. Colormetric method for the determination of sugars and related substances. Anal. Chem. 28:350–356.
12. Freimer, E. H. 1967. Type-specific polysaccharide antigens of group B streptococci. J. Exp. Med. 125:381–392.
13. Gelfand, H. M., J. P. Fox, D. R. LeBlanc, and L. Elveback. 1960. Studies on the development of natural immunity to poliomyletis in Louisiana. V. Passive transfer of polioantibody from mother to fetus, and natural decline and disappearance of antibody in the infant. J. Immunol. 85:46–55.
14. Goebel, W. F., and O. T. Avery. 1931. Chemo-Immunological studies on conjugated carbohydrate-proteins. IV. The synthesis of the p-aminobenzyl ether of the soluble specific substance of type III pneumococcus and its coupling with protein. J. Exp. Med. 54:431–436.
15. Gray, B. M. 1979. ELISA methodology for polysaccharide antigens: protein coupling of polysaccharides for adsorption to plastic tubes. J. Immunol. Methods 28:187–192.
16. Hobbs, J. R., and J. A. Davis. 1967. Serum gamma-G globulin levels and gestational age in premature babies. Lancet 493:757–759.
17. Insel, R. A., and P. W. Anderson. 1986. Oligosaccharide-protein conjugate vaccines induce and prime for oligoclonal IgG antibody responses to the Haemophilus Influenzae b capsular polysaccharide in human infants. J. Exp. Med. 163:262–269.
18. Jennings, H. J., and C. Lugowski. 1981. Immunochemistry of groups A, B, and C meningococcal polysaccharide tetanus toxoid conjugates. J. Immunol. 127:1011:1018.
19. Jennings, H. J., C. Lugowski, and F. E. Ashton. 1984, Conjugation of meningococcal lipopolysaccharide R-type oligosaccharides to tetanus toxoid as a route to a potential vaccine against group B Neisseria meningitidis. Infect. Immun. 43:407–412.
20. Jennings, H. J., K. G. Rosell, E. Katzenellenbogen, and D. L. Kasper. 1983. Structural determination of the capsular polysaccharide antigen of type II group B Streptococcus. J. Biol. Chem. 258:1793–1798.
21. Kasper, D. L., C. J. Baker, B. Galdes, E. Katzenellenbogen, and H. J. Jennings. 1983. Immunochemical analysis and immunogenicity of the type II group B streptococcal capsular polysaccharide. J. Clin. Invest. 72:260–269.
22. Lagergard, T., J. Shiloach, J. B. Robbins, and R. Schneerson. 1990. Synthesis and immunocological properties of conjugates composed of group B Streptococcus type III capsular polysaccharide covalently bound to tetanus toxoid. Infect. Immun. 58:687–694.
23. Lancefield, R. C. 1972. Cellular antigens of group B streptococci, p. 57–65. In L. W. Wannamaker and J. M. Matson (ed.), Streptococci and streptococcal diseases: recognition, understanding, and management. Academic Press, Inc. New York.
24. Lancefield, R. C., M. McCarty, and W. N. Everly. 1975. Multiple mouse-protective antibodies directed against group B streptococci. J. Exp. Med. 142:165–179.

25. Lowry, O. H., N. J. Rosebrough, A. L. Farr, and R. J. Randall. 1951. Protein measurement with the Folin phenol reagent. J. Biol. Chem. 193:265–275.
26. Michon, F., E. Katzenellenbogen, D. L. Kasper, and H. L. Jennings. 1987. Structure of the complex group-specific polysaccharide of group B Streptococcus. Biochemistry 26:476–486
27. Paoletti, L. C., D. L. Kasper, F. Michon, J. DiFabio, K. Holme, H. J. Jennings, and M. R. Wessels. 1990. An oligosaccharide-tetanus toxoid conjugate vaccine against type III group B Streptococcus. J. Biol. Chem. 265:18278–18283.
28. Paoletti, L. C., D. L. Kasper, F. Michon, H. J. Jennings, T. D. Tosteson, and M. R. Wessels. 1992. Effects of chain length on the immunogenicity in rabbits of group B Streptococcus type III oligosaccharide-tetanus toxoid conjugates. J. Clin. Invest. 89:203–209.
29. Schneerson, R. O. Barrera, A. Sutton, and J. B. Robbins. 1980. Preparation, characterization and immunogenicity of Haemophilus influenzae type b polysaccharide-protein conjugates. J. Exp. Med. 152:361–376.
30. Svenson, S. B. and A. A. Lindberg. 1979. Coupling of acid-labile Salmonella specific oligosaccharides to macromolecular carriers. J. Immunol. Methods 25:323–335.
31. Walsh, J. A., and S. Hutchins. 1989. Group B streptococcal disease: its importance in the developing world and prospect for prevention with vaccines. Pediatr. Infect. Dis. J. 8:271–276.
32. Warren, L. 1959. The thiobarbituric acid assay of sialic acids. J. Biol. Chem. 234:1971–1975.
33. Wessels, M. R., L. C. Paoletti, D. L. Kasper, J. L. DiFabio, F. Michon, K. Holme, and H. J. Jennings. 1990. Immunogenicity in animals of a polysaccharide-protein conjugate vaccine against type III group B Streptococcus, J. Clin. Invest. 86:1428–1433.
34. Zigterman, J. W. J., J. E. G. van Dam, H. Snippe, F. T. M. Rottsveel, M. Jansze, J. M. N. Willers, J. P. Kamerling, and J. F. G. Vliegenthart. 1985. Immunogenic properties of octasaccharide-protein conjugates derived from Klebsiella serotype II capsular polysaccharide. Infect. Immun. 47:421–428.
35. Wessels, M. R., J. L. D;Fabio, V. J. Benedi, D. L. Kasper, F. Michon, J-R. Brisson, J.Jelinkova and H. J. Jennings 1991. Structural Determination and Immunochemical Characterization of the Type V Group B Streptococcus Capsular Polysaccharide. Journal of Biological Chemistry 266:8714–8719.

While we have hereinbefore described a number of embodiments of this invention, it is apparent that the basic constructions can be altered to provide other embodiments which utilize the methods of this invention. Therefore, it will be appreciated that the scope of this invention is defined by the claims appended hereto rather than by the specific embodiments which have been presented hereinbefore by way of example.

We claim:

1. An antigenic conjugate molecule comprising a type V capsular polysaccharide derived from a Group B streptococcus bacteria and a protein component wherein two or more side chains terminating in sialic acid residues of the polysaccharide component are each linked through a secondary amine bond to protein and wherein the molecular weight of the polysaccharide used for conjugation is at least 5000 daltons.

2. The conjugate molecule according to claim 1 wherein prior to conjugation between 5 and 50% of the terminal sialic acid residues of said polysaccharide were available to be linked to protein.

3. The conjugate molecule according to claim 2 wherein prior to conjugate between 5 and 25% of the terminal sialic acid residues of said polysaccharide were available to be linked to protein.

4. The conjugate molecule according to claim 3 wherein prior to conjugation between 5 and 10% of the terminal sialic acid residues of said polysaccharide were available to be linked to protein.

5. The conjugate molecule according to claim 1 wherein the antigenic conjugate molecule is capable of being filter sterilized through a 0.2 micron filter.

6. The conjugate molecule according to claim 1 wherein the polysaccharide component has a molecular weight of between about 5,000 and 1,000,000 daltons.

7. The conjugate molecule according to claim 6 wherein the polysaccharide component has a molecular weight of between about 50,000 and 500,000 daltons.

8. The conjugate molecule according to claim 1 wherein about 25% of the terminal sialic acid residues of each polysaccharide are linked to protein.

9. The conjugate molecule according to claim 7 wherein the polysaccharide component has a molecular weight of between about 100,000 and 300,000 daltons.

10. The conjugate molecule according to claim 8 wherein the polysaccharide component has a molecular weight of about 200,000 daltons.

11. The conjugate molecule according to claim 1 wherein the protein is selected from the group consisting of tetanus toxoid, diphtheria toxoid and CRM (Cross Reactive Material) 197.

12. A method of preparing a conjugate molecule of a capsular polysaccharide of Group B streptococcus type V bacteria and a protein comprising;
(a) subjecting the Group B streptococcus type V capsular polysaccharide to periodate oxidation sufficient to introduce an aldehyde group into two or more terminal sialic acid residues linked to the backbone of the polysaccharide;
(b) coupling the oxidized Group B streptococcus type V capsular polysaccharide to a protein through reductive amination to generate a secondary amine bond between the capsular polysaccharide and the protein.

13. The method according to claim 12 wherein between about 5 and 50% of the sialic acid residues of said polysaccharide are oxidized to form aldehyde groups capable of coupling to protein.

14. The method according to claim 13 wherein between about 5 and 25% of the sialic acid residues of said polysaccharide are oxidized to form aldehyde groups capable of coupling to protein.

15. The method according to claim 14 wherein between about 5 and 10% of the sialic acid residues of said polysaccharide are oxidized to form aldehyde groups capable of coupling to protein.

16. The method according to claim 12 wherein between about 5 and 50% of the sialic acid residues of said polysaccharide are covalently linked to protein.

17. The method according to claim 16 wherein between about 5 and 25% of the sialic acid residues of said polysaccharide are covalently linked to protein.

18. The method according to claim 17 wherein between about 5 and 10% of the sialic acid residues of said polysaccharide are covalently linked to protein.

19. The method according to claim 12 wherein the polysaccharide is GBS type V and wherein about 25% of the terminal sialic acid residues of said polysaccharide are linked to protein.

20. A conjugate molecule prepared according to the method of claim 12.

21. A vaccine comprising the conjugate molecule according to claim 1.

22. A multivalent vaccine comprising the conjugate molecule according to claim 1 and at least one other immunogenic molecule capable of eliciting the production of antibodies to a pathogenic substance other than Group B streptococcus type V.

23. The multivalent vaccine according to claim 22 wherein the other immunogenic molecules are capable of eliciting the production of antibodies to pathogens selected from the group consisting of Group B streptococcus types Ia, Ib, II, III, IV and V, Haemophilus influenzae type b and E. coli type K1.

24. The multivalent vaccine according to claim 23 wherein the other immunogenic molecules are capable of eliciting the production of antibodies to pathogens selected from the group consisting of Group B streptococcus types Ia, Ib, II, III, Haemophilus influenzae type b and E. coli type K1.

25. The multivalent vaccine according to claim 24 wherein the other immunogenic molecules are capable of eliciting the production of antibodies to pathogens selected from the group consisting of Group B streptococcus types Ia, Ib, II, III and E. coli type K1.

26. The multivalent vaccine according to claim 25 wherein the other immunogenic molecules are capable of eliciting the production of antibodies to pathogens selected from the group consisting of Group B streptococcus types Ia, Ib, II, III.

27. A method of immunizing humans wherein a vaccine comprising the conjugate molecule according to claim 1 is administered in an immunogenic amount to humans.

28. A method of immunizing adults wherein a vaccine comprising the conjugate molecule according to claim 1 is administered in an immunogenic amount to a person at risk for being infected by Group B streptococcus type V.

29. The method according to claim 28 wherein the vaccine is administered to a person whose immune system is suppressed.

30. The method according to claim 29 wherein immunosuppression is due to diseases selected from the group consisting of cancer or diabetes.

31. The method according to claim 30 wherein said vacine is administered in a pharmaceutically acceptable carrier.

32. A method of immunizing dairy herds against bovine mastitis consisting of administering a vaccine comprising the conjugate molecule according to claim 1 in an immunogenic amount to dairy cows.

\* \* \* \* \*